(12) United States Patent
Bani-Hashemi

(10) Patent No.: US 9,789,337 B2
(45) Date of Patent: Oct. 17, 2017

(54) COMBINED IMAGING MODALITIES FOR RADIATION TREATMENT PLANNING

(75) Inventor: Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1009 days.

(21) Appl. No.: 13/269,324

(22) Filed: Oct. 7, 2011

(65) Prior Publication Data

US 2013/0090547 A1    Apr. 11, 2013

(51) Int. Cl.
*A61B 5/055* (2006.01)
*A61N 5/10* (2006.01)

(52) U.S. Cl.
CPC ........... *A61N 5/1039* (2013.01); *A61B 5/055* (2013.01); *A61N 2005/105* (2013.01); *A61N 2005/1054* (2013.01); *A61N 2005/1091* (2013.01); *A61N 2005/1094* (2013.01)

(58) Field of Classification Search
CPC . G01R 33/4808; A61B 6/4417; A61B 6/5229; A61B 5/055; A61N 2005/105; A61N 2005/1054; A61N 2005/1091; A61N 2005/1094; A61N 5/1039
See application file for complete search history.

(56) References Cited

U.S. PATENT DOCUMENTS

| | | | | |
|---|---|---|---|---|
| 3,720,817 A | * | 3/1973 | Dinwiddie | 600/1 |
| 4,123,660 A | * | 10/1978 | Horwitz | 378/65 |
| 5,820,553 A | * | 10/1998 | Hughes | 600/426 |
| 2003/0007601 A1 | * | 1/2003 | Jaffray et al. | 378/65 |
| 2007/0244386 A1 | * | 10/2007 | Steckner | A61B 17/2256 600/411 |
| 2009/0080594 A1 | * | 3/2009 | Brooks | A61B 6/502 378/4 |
| 2010/0053208 A1 | * | 3/2010 | Menningen et al. | 345/619 |
| 2011/0309242 A1 | * | 12/2011 | Maltz | G21H 5/02 250/252.1 |

FOREIGN PATENT DOCUMENTS

WO    WO 2006/018761 A1 *  2/2006    ........... A61N 5/00

OTHER PUBLICATIONS

XiaoShen Wang et al., "A comparative study of three CT and MRI registration algorithms in nasopharyngeal carcinoma", Journal of Applied Clinical Medical Physics, vol. 10, No. 2 (2009), 9pgs.

"The Role of PET/CT in Radiation Treatment Planning for Cancer Patient Treatment", IAEA International Atomic Energy Agency, Oct. 2008, IAEA-TECDOC-1603 (cover 4 + contents 1 + pp. 1-33, total 38 pages).

* cited by examiner

*Primary Examiner* — Ruth S Smith

(57) ABSTRACT

A system includes acquisition of a first three-dimensional image of a patient volume using a magnetic resonance imaging scanner, acquisition of a second three-dimensional image of the patient volume using cone beam radiation emitted by the linear accelerator, and generation of a radiation treatment plan based on the first image and the second image.

14 Claims, 5 Drawing Sheets

COMBINED IMAGING MODALITIES FOR RADIATION TREATMENT PLANNING

BACKGROUND

Field

The embodiments described below relate generally to the delivery of therapeutic radiation to a patient. More specifically, some embodiments are directed to the generation of radiation treatment plans.

Description

According to conventional radiation treatment, a beam of radiation is directed toward a target volume (e.g., a cancerous tumor) located within a patient. The radiation beam delivers a predetermined dose of therapeutic radiation to the target volume according to an established treatment plan. The delivered radiation kills cells of the target volume by causing ionizations within the cells or other radiation-induced cell damage.

Treatment plans are designed to deliver a particular radiation dose to a target volume, while ensuring that surrounding healthy tissue does not receive an unsafe dose. Treatment plan design therefore requires the identification of various tissues within a patient volume (i.e., to identify targets, surrounding tissue and organs-at-risk), and the electron densities of the various tissues (i.e., to calculate the dose delivered to those tissues).

Computed tomography (CT) imaging may be employed to acquire an image of a patient volume for treatment planning purposes. CT images may provide a level of clarity suitable for tumor and organ delineation. Moreover, CT images provide a good representation of the electron densities of imaged tissues. Magnetic resonance (MR) imaging typically provides clearer differentiation of tissue types in comparison to CT imaging, and is therefore particularly suitable for tumor and organ delineation. However, MR images do not adequately represent the electron density of the imaged tissues.

Some conventional systems include acquisition of a CT image and an MR image of a patient volume, and combination of the CT image and the MR image. A treatment plan may then be designed based on the combined image, with the initial delineation step being performed based on the MR data and the dose calculation step being performed based on the CT data. A positron emission tomography (PET) image may also be acquired and combined with the CT image and the MR image in order to assist in identifying malignancies.

Facilities using the foregoing systems require an MR scanner and a CT scanner, in addition to a linear accelerator (LINAC) which will be used to execute the designed treatment plan. Due to the attendant costs, it has been proposed to design treatment plans based solely on MR images. According to this proposal, an MR image is used to delineate tissues, and each tissue type is assigned an electron density based on predefined values. The assigned electron densities are then used for the dose calculations described above. However, the electron densities for particular types of tissues will vary from patient to patient, so doses calculated in this manner for a given patient will be less accurate than doses calculated using electron densities which are determined from a CT image of the patient.

Systems are needed to facilitate treatment planning while addressing one or more shortcomings of existing systems.

SUMMARY

To address at least the foregoing, some embodiments provide a system, method, apparatus, and means to acquire a first three-dimensional image of a patient volume using a magnetic resonance imaging scanner, acquire a second three-dimensional image of the patient volume using cone beam radiation emitted by the linear accelerator, and generate a radiation treatment plan based on the first image and the second image.

In some aspects, a plurality of sub-regions is defined within the patient volume based on the first three-dimensional image, and a radiation dose associated with each of the plurality of sub-regions is determined based on the second three-dimensional image. Some aspects include acquisition of a third three-dimensional image using a positron emission tomography scanner, where the treatment plan is generated based on the first image, the second image and the third image.

According to some aspects, a treatment isocenter of the patient is recorded based on the first three-dimensional image, and the treatment isocenter of the patient is registered with the isocenter of the linear accelerator. Moreover, the second three-dimensional image is acquired while the treatment isocenter of the patient is registered with the isocenter of the linear accelerator.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
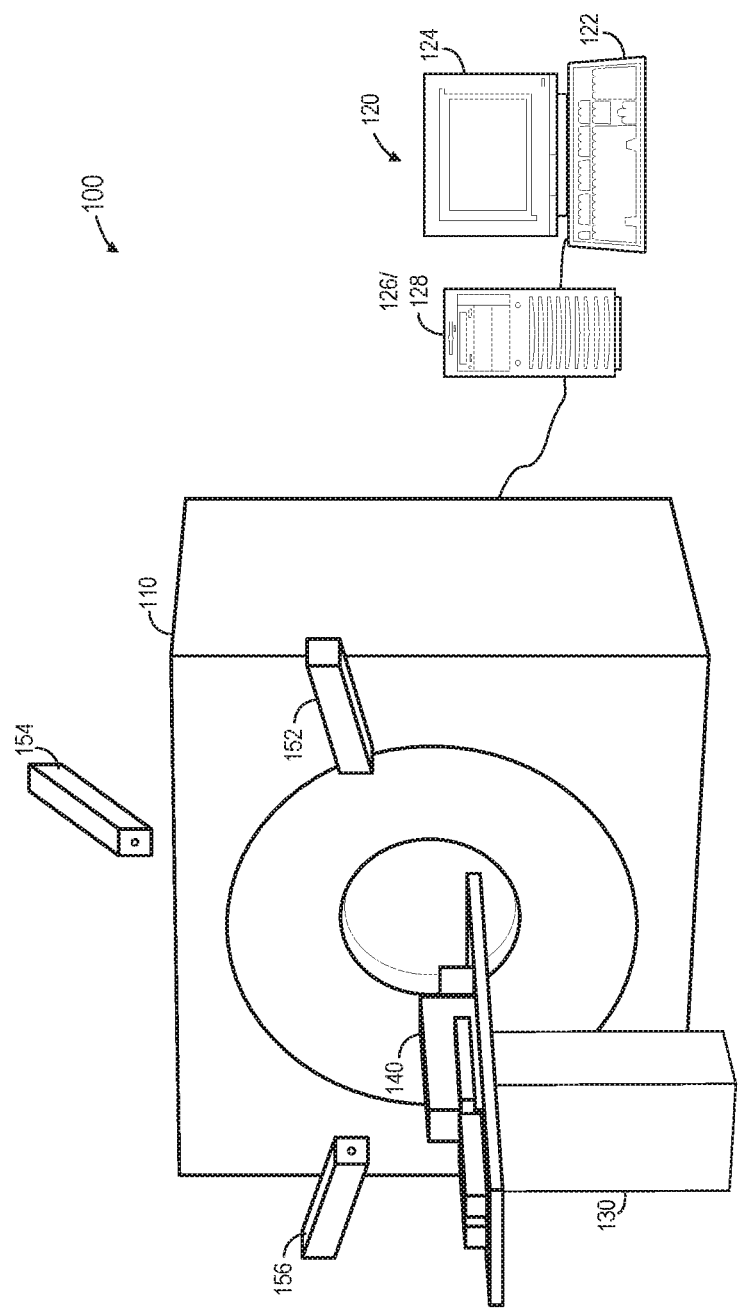
FIG. 1 is a perspective view of a magnetic resonance imaging system according to some embodiments.

FIG. 1 illustrates MRI system 100 for generating images of patient volumes. MRI system 100 includes MRI scanner 110, operator console 120 and table 130. The main components (not shown) of MRI scanner 110 include a main magnet to polarize atoms within the patient, shim coils for correcting inhomogeneities in the magnetic field of the main magnet, a radio frequency system to excite the sample and detect the resulting signal, and gradient coils to localize the resulting signal.

In operation, and under control of an operator operating console 120, patient 140 is placed on table 130 and is moved into a magnetic field generated by MRI scanner 110. The radio frequency system of scanner 110 uses radio frequency fields to systematically alter the alignment of thusly-polarized atoms of patient 140. Such operation causes the atomic nuclei to produce detectable signals, and this information is used construct one or more images of the scanned volume of the patient. To obtain three-dimensional images, the gradient coils provide strong magnetic field gradients in each direction, which cause nuclei at different locations to rotate at different speeds and to produce different signals.

A magnetic resonance image exhibits good contrast between the different soft tissues of the body, compared with other medical imaging techniques such as CT or X-rays. Moreover, unlike CT scans or traditional X-rays, magnetic resonance imaging does not use ionizing radiation.

Operator console 120 includes input device 122 for receiving instructions from an operator and output device 124, which may be a monitor for presenting operational parameters of scanner 110 and for displaying images acquired thereby. Input device 122 and output device 124 are coupled to processor 126 and storage 128. Processor 126 may execute program code stored in storage 128 to perform any of the operations, and/or to cause scanner 110 to perform any of the operations, described herein.

Storage 128 may also store program code executable to allow a clinician to evaluate the MRI image(s) and to identify a treatment isocenter. A treatment isocenter is a point in a patient volume through which a central beam of treatment radiation should pass. For example, the treatment isocenter may comprise the center point of a tumor identified in the MRI images.

System 100 also includes lasers 152, 154 and 156. According to some embodiments, console 120 positions lasers 152, 154 and 156 to emit light beams toward patient 140 which, if imagined to extend unmolested into the patient volume, would all intersect at the treatment isocenter. The skin of patient 140 may be marked (e.g., with tattoos) at the points at which each beam intercepts the skin, in order to facilitate future registration of the treatment isocenter with a LINAC isocenter. Any other known system (e.g., implanted fiducials, surface photogrammetry) may be employed to achieve such registration according to some embodiments.

Figure 2:
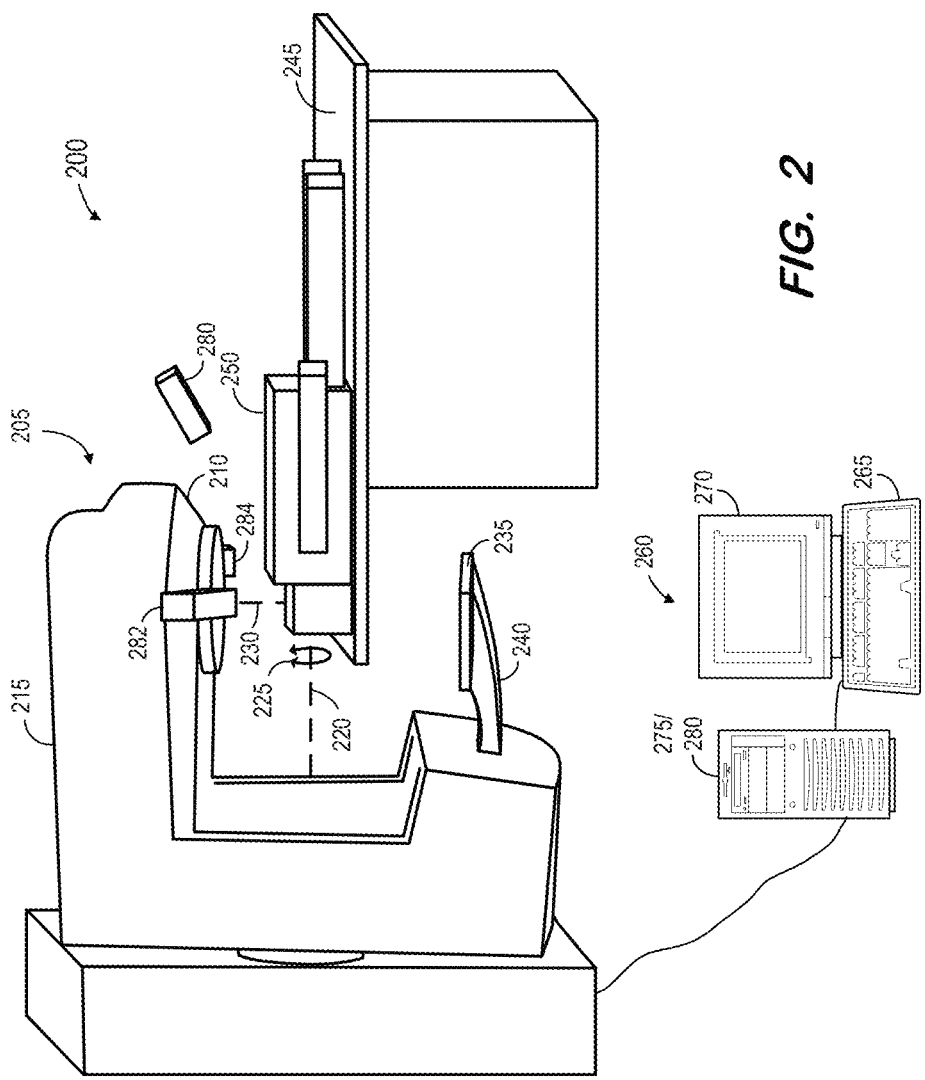
FIG. 2 is a perspective view of a radiation treatment system according to some embodiments.

FIG. 2 illustrates radiation treatment system 200 pursuant to some embodiments. Radiation treatment system 200 includes LINAC 205, table 245, operator console 260 and lasers 280, 282, and 284. The elements of radiation treatment system 200 may be used to deliver radiation to a target volume of patient 250 according to a radiation treatment plan. The elements may also be used to generate three-dimensional images of the target volume using cone beam CT techniques.

Linac 205 generates and emits the radiation, and is primarily composed of treatment head 210 and gantry 215. Treatment head 210 includes a beam-emitting device (not shown) for emitting one or more radiation beams during treatment, calibration, and/or other scenarios. An emitted radiation beam may comprise electron, photon or any other type of radiation. According to some embodiments, the radiation beam exhibits energies of more than 1 MeV (i.e., megavoltage radiation) and/or between 50 and 150 keV (i.e., kilovoltage radiation). Also included within treatment head 210 is a beam-shielding device, or collimator (not shown) for shaping the beam.

Treatment head 210 is coupled to a projection of gantry 215. Gantry 215 is rotatable around gantry axis 220 before, during and after imaging and/or radiation treatment. As indicated by arrow 225, gantry 215 may rotate clockwise or counter-clockwise according to some embodiments. Rotation of gantry 215 serves to rotate treatment head 210 around axis 220.

During imaging or radiation treatment, a radiation beam is emitted from treatment head 210 as a divergent beam (i.e., a cone). The beam is emitted towards an isocenter of linac 205. The isocenter is located at the intersection of beam axis 230 and gantry axis 220. Due to divergence of the radiation beam and the shaping of the beam by the aforementioned beam-shaping devices, the beam may deliver radiation to a volume of beam object 250 rather than only to the isocenter.

During treatment, linac 205 may be operated so that each treatment beam emitted thereby exhibits a desired intensity (e.g., represented in monitor units (MU)) and aperture (i.e., a cross-sectional shape determined at least in part by the above-mentioned collimator), and is delivered from a desired gantry angle. The intensity, aperture and gantry angle of a beam are specified by a treatment plan, and control software may configure linac 205 to automatically execute such a treatment plan by delivering beams of the desired intensities and shapes from the desired angles at desired moments.

Table 245 supports beam object 250 during imaging and/or radiation treatment. Table 245 may be adjustable to assist in positioning a treatment isocenter of beam object 250 at the isocenter of linac 205. Table 245 may also be used to support devices used for such positioning, for calibration and/or for verification.

Lasers 280, 282 and 284 may emit beams which intersect, if unimpeded, at the isocenter of linac 205. Lasers 280, 282 and 284 may share the same relative positioning as laser 152, 154 and 156 of system 100. Accordingly, if a patient marked with tattoos as described above is placed such that the beams from lasers 280, 282 and 284 intercept the tattoos, then the treatment isocenter will be located at the isocenter of linac 205. Alignment of these two positions based on physical features (i.e., the tattoos) is referred to as registration.

Imaging device 235 may acquire images before, during and/or after radiation treatment. For example, imaging device 235 may be used to acquire images used to generate a treatment plan, and for verification and recordation of a target volume position and of an internal patient portal to which radiation is to be delivered.

Imaging device 235 may be attached to gantry 215 in any manner, including via extendible and retractable housing 240. Rotation of gantry 215 may cause treatment head 210 and imaging device 235 to rotate around the isocenter such that the isocenter remains located between treatment head 210 and imaging device 235 during the rotation.

Imaging device 235 may comprise any system to acquire an image based on received megavoltage photon radiation. In a case that linac 205 is capable of producing kilovoltage photon radiation via beamline modification or other techniques (e.g., via a separate rotatable head for emitting kilovoltage radiation), imaging device 235 may also acquire images based on such kilovoltage radiation. In some embodiments, imaging device 235 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 235 converts received photons to electrical charge without requiring a scintillator layer. The photons are absorbed directly by an array of amorphous selenium photoconductors. The photoconductors convert the photons directly to stored electrical charge. Imaging device 235 may also comprise a CCD or tube-based camera. Such an imaging device 235 may include a light-proof housing within which are disposed a scintillator, a mirror, and a camera.

The charge developed and stored by imaging device 235 represents radiation intensities at each location of a radiation field produced by a beam emitted from treatment head 210. Since object 250 is located between treatment head and imaging device 235, the radiation intensity at a particular location represents the attenuative properties of tissues along a divergent line between a radiation source in treatment head 210 and the particular location. The set of radiation intensities acquired by imaging device 235 may therefore comprise a two-dimensional projection image of these tissues.

Operator console 260 includes input device 265 for receiving instructions from an operator and output device 270, which may be a monitor for presenting operational parameters of linac 205 and imaging device 235, interfaces for receiving instructions and/or acquired images. Output device 270 may also present a two-dimensional projection image, a three-dimensional megavoltage (or kilovoltage) cone beam image constructed based on several two-dimensional projection images and/or two-dimensional "slice" images determined from the three-dimensional image.

Input device 265 and output device 270 are coupled to processor 275 and storage 280. Processor 275 may execute program code to perform any of the operations, and/or to cause linac 205 to perform any of the operations, described herein.

Storage 280 may store program code to generate and/or modify a treatment plan according to some embodiments. Such code may comprise the SyngoRT™ suite or the KONRAD™ treatment planning system sold by Siemens Medical Solutions®. Accordingly, storage 280 may also store radiation treatment plans in accordance with any currently- or hereafter-known format. The treatment plans may comprise scripts that are automatically executable by elements of system 200 to provide radiation therapy fractions. Each fraction of each treatment plan may require a patient to be positioned in a particular manner with respect to treatment head 210.

Operator console 260 may be in a room other than treatment system 200, in order to protect its operator from radiation. For example, treatment system 200 may be heavily shielded, such as a concrete vault, to shield the operator from radiation generated by linac 205.

Figure 3:
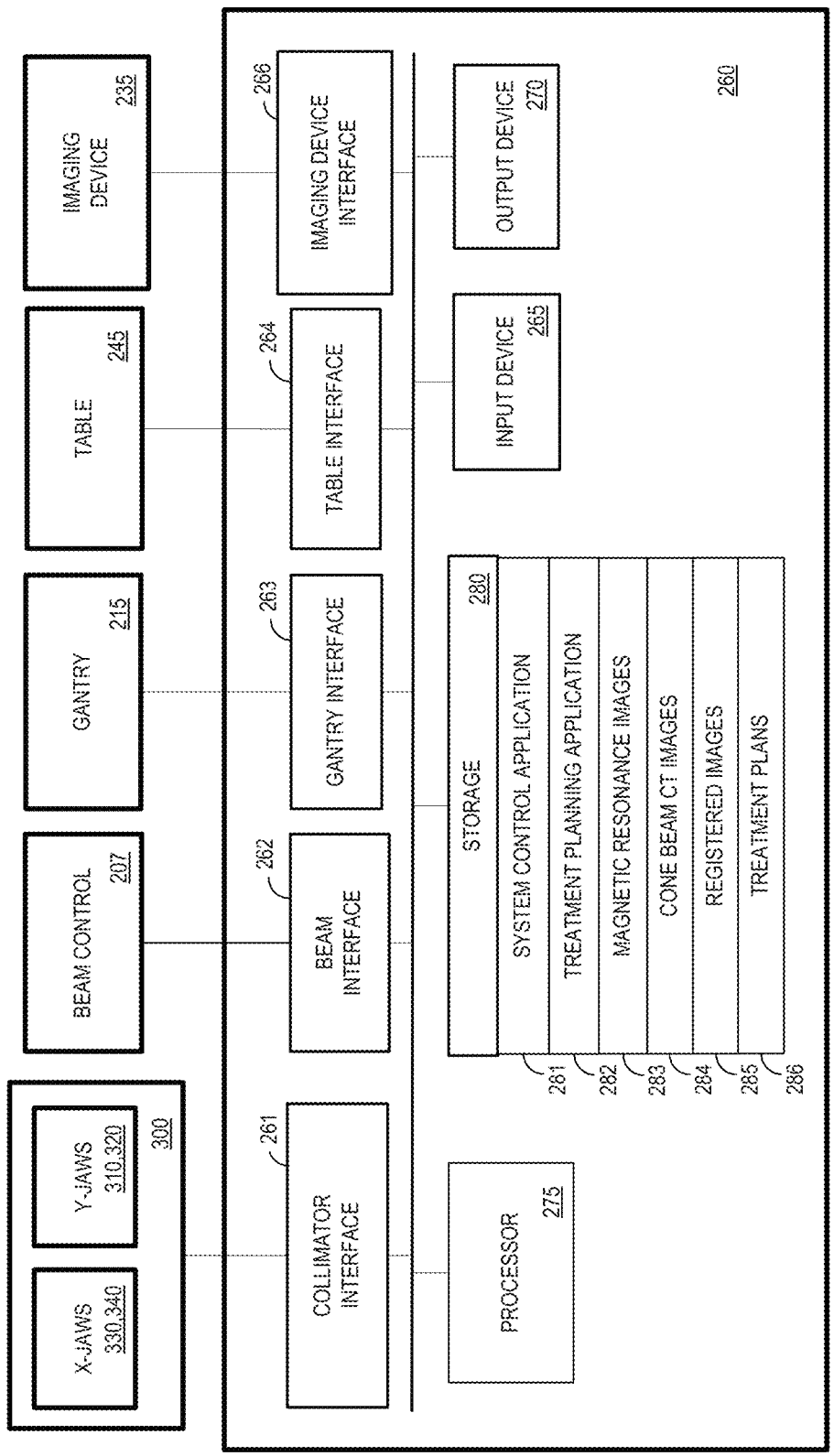
FIG. 3 is a block diagram of the internal architecture of a radiation treatment system according to some embodiments.

FIG. 3 is a block diagram of elements of treatment system 300 according to some embodiments. The illustrated elements may be implemented by any suitable combination of hardware, software and/or firmware. Operator console 260 may be implemented by one or more separate computing systems.

As shown, operator console 260 includes several elements for interfacing with other elements of treatment system 200. Specifically, operator console 260 includes collimator interface 261, beam interface 262, gantry interface 263, table interface 264, and imaging device interface 266. Operator console 260 may control the various elements through the interfaces and based on instructions received from processor 275.

Collimator interface 261 may be used to control the opening, closing and rotation of collimator 300. Beam interface 262 may control beam-controlling elements 207 of linac 205 based on desired beam characteristics. In particular, beam interface 262 may control trigger signals for controlling an injector current and RF power signal to generate a treatment beam or an imaging beam having a particular energy.

Interfaces 261, 262, 263, 264 and 266 may comprise dedicated hardware and/or software interfaces, and one or more of interfaces 261, 262, 263, 264 and 266 may be implemented by a single interface. For example, interfaces 261 through 263 may be implemented by a single Ethernet interface and interfaces 264 and 266 may be implemented by proprietary interfaces for interfacing with table 245 and imaging device 235.

Processor 275 executes processor-executable program code stored in storage 280 to provide operation according to some embodiments. Storage 280 may comprise any tangible medium, including but not limited to a fixed disk, a floppy disk, a CD-ROM, a DVD-ROM, a Flash drive, or a magnetic tape. The program code may comprise treatment planning application 281 to generate one or more of treatment plans 285 as mentioned above, and system control application 282 to execute one of treatment plans 285 according to some embodiments.

As will be described below, a treatment plan may be generated based on magnetic resonance images 283 and cone beam CT images 284 of storage 280. For example, MRI scanner 110 may acquire a three-dimensional magnetic resonance image of a patient volume, which is then stored in storage 280. Next, system 200 may acquire a cone beam CT image of the patient volume and store the cone beam CT image in storage. A treatment plan may then be generated for the patient volume based on the two images. Additional details of such a process will be provided below. According to some embodiments, a separate computer system including a processor (e.g., a dedicated planning system) may execute program code to generate treatment plans as described herein.

Treatment plans 285 may conform to any currently- or hereafter-known format. Treatment plans 285 may comprise scripts that are automatically executable by linear accelerator 205 and treatment table 245 to provide radiation therapy fractions. Each of treatment plans 285 may require a patient to be positioned in a particular manner with respect to treatment head 210.

A hardware environment according to some embodiments may include less or more elements than those shown in FIGS. 1 through 3. In addition, embodiments are not limited to the illustrated devices and/or to the illustrated environment.

Figure 4:
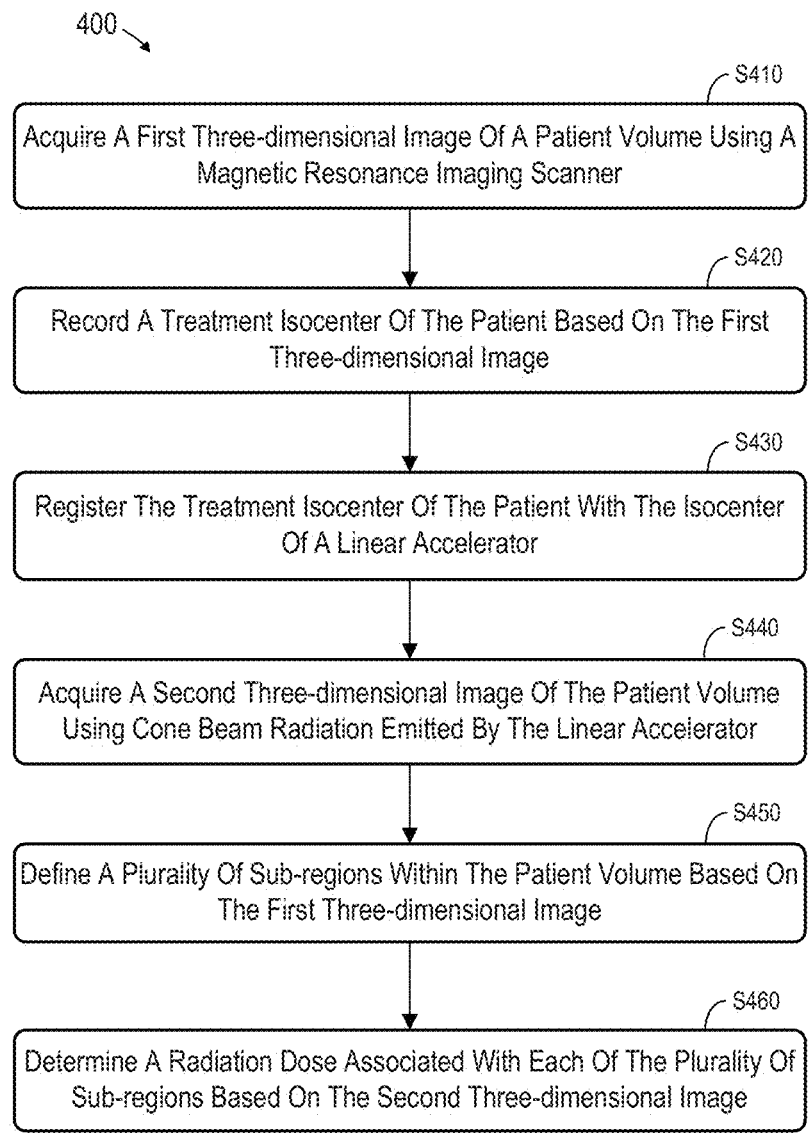
FIG. 4 comprises a flow diagram illustrating a process according to some embodiments.

FIG. 4 is a flow diagram of process 400 according to some embodiments. Process 400 and the other processes described herein may be performed using any suitable combination of hardware, software or manual means. Software embodying these processes may be stored by any tangible medium, including but not limited to a fixed disk, a floppy disk, a CD-ROM, a DVD-ROM, a Flash drive, or a magnetic tape. Examples of these processes will be described below with respect to the elements of systems 100 and 200, but embodiments are not limited thereto.

Initially, at S410, a three-dimensional image of a patient volume is acquired using a magnetic resonance imaging scanner. Any system employing the basic principles of magnetic resonance imaging may be employed at S410. As described above, the image might be acquired by applying a strong magnetic field, selectively activating radio frequency fields, and detecting resulting signals emitted from the patient volume. Magnetic field gradients are provided to produce three-dimensional location information. The acquired three-dimensional image may be stored in storage 128 for later transfer to a treatment planning system.

A treatment isocenter of the patient is recorded at S420 based on the three-dimensional image acquired at S410. In some embodiments, a clinician operates console 120 to evaluate the three-dimensional image to identify the treatment isocenter. Such evaluation may include review of two-dimensional slices of the three-dimensional image. In one example, the clinician locates a tumor in the three-dimensional image and chooses the center of the tumor as the treatment isocenter. This location is then recorded (i.e. saved) for use at S430.

Specifically, the location is used to register the treatment isocenter with the isocenter of a linear accelerator at S430. Registration at S430 generally includes placing the treatment isocenter at a known distance and direction from the linac isocenter. According to some embodiments, and as described above, lasers 152, 154 and 156 are positioned to emit light beams toward patient 140 which, if imagined to extend unmolested into the patient volume, would all intersect at the treatment isocenter. Tattoos are placed on the points at which each beam intercepts the patient's skin.

The patient is then moved to a treatment room including a linac (e.g., linac 205) and lasers (e.g., lasers 280, 282 and 284) positioned such that their beams intersect at the isocenter of linac 205. The patient is placed such that the beams from lasers 280, 282 and 284 intercept the tattoos, in order to register the treatment isocenter with the isocenter of linac 205. Additional steps (e.g., portal imaging, etc.) to fine-tune the registration may be executed as is known in the art.

Next, at S440, a second three-dimensional image of the patient volume is acquired using cone beam radiation emitted by a linear accelerator. According to some embodiments, the patient remains at the position established at S430 during S440. Although kilovoltage radiation may be used at S440, such as in conventional CT scanning, megavoltage radiation is better suited for acquiring images representing electron density because such imaging is primarily based on Compton interaction. In contrast, kilovoltage imaging results from a mixture of Compton and photoelectric interaction.

As is known, acquisition of a three-dimensional cone beam CT image includes rotating gantry 215 to various positions around the patient volume and, at each position, emitting radiation to acquire a two-dimensional projection image of the patient volume. A reconstruction algorithm is applied to the acquired projection images to generate the three-dimensional cone beam CT image.

In view of the imaging geometry of linac 205, and the limited size of imaging device 235, the field of view of the projection images might not be large enough to include the entire patient and the reconstructed image will be truncated as a result. However, dose calculation requires the electron density of all tissues with which the beam will interact.

Accordingly, in some embodiments, S440 proceeds in an extended field of view acquisition mode, as is known in the art. Generally, an imaging panel of the imaging device is offset laterally and projection images are acquired as described above. The imaging panel of the linear accelerator is positioned so that the central ray of cone beam radiation emitted from the linear accelerator does not intersect the center of the imaging panel during acquisition of the projection images.

The three-dimensional magnetic resonance image facilitates the delineation of tissues, the three-dimensional cone beam CT image provides electron density information, and the images may be spatially related to one another due to the registration at S430. Accordingly, as will be described below with respect to S450 and S460, the three-dimensional magnetic resonance image and the three-dimensional cone beam CT image may be used to generate a treatment plan according to some embodiments. Embodiments are not limited to S450 and S460.

A plurality of sub-regions within the patient volume are defined at S450 based on the first three-dimensional image. The regions may be defined by a clinician operating console 120, console 260, or any other computing device. For example, the first three-dimensional image and/or a slice thereof is displayed and the clinician (or an automated algorithm) defines various sub-regions of the patient volume using the displayed image.

Figure 5:
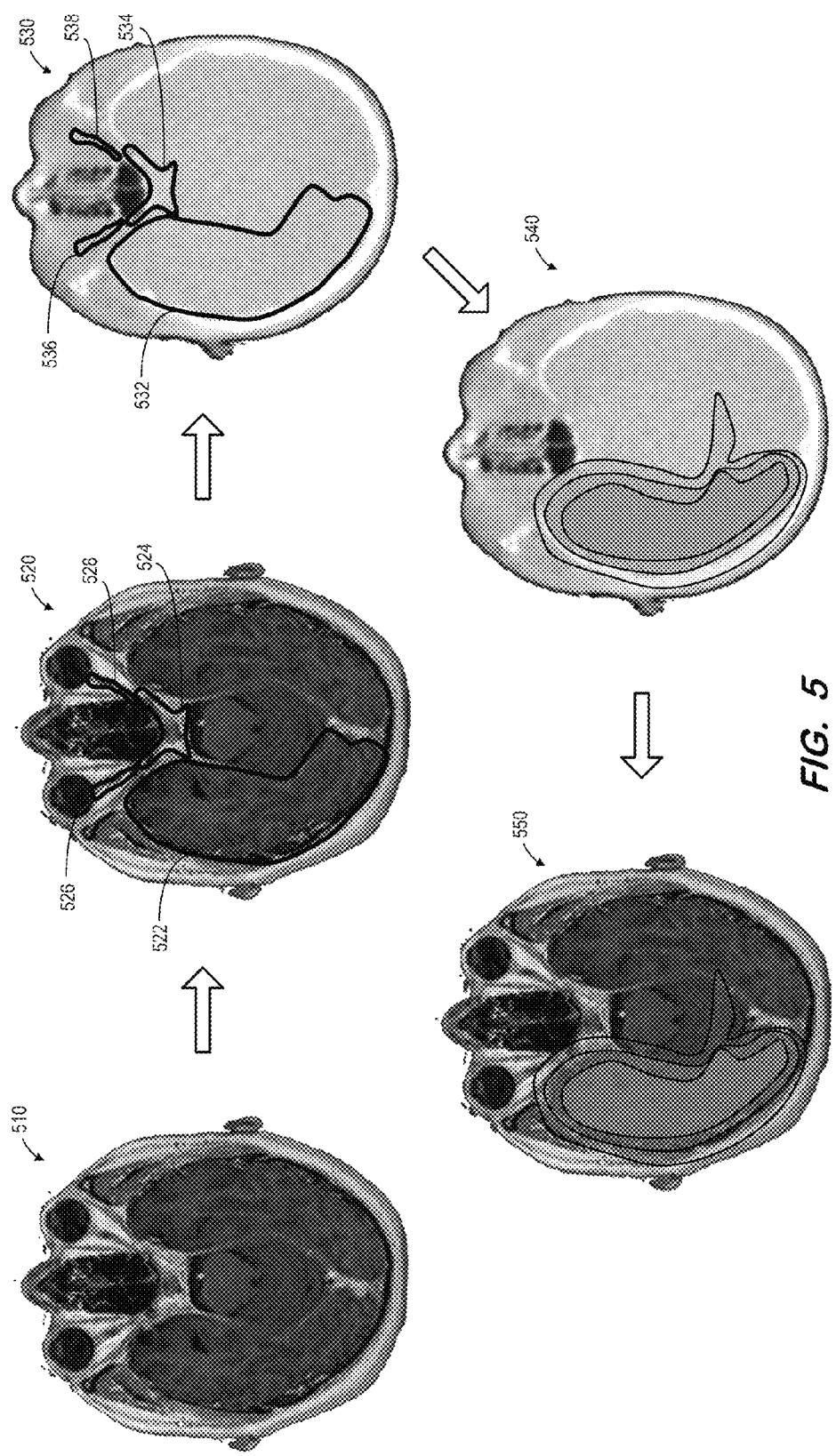
FIG. 5 illustrates the generation of a radiation treatment plan based on a magnetic resonance image and a cone beam CT image according to some embodiments.

FIG. 5 shows slice 510 of a three-dimensional magnetic resonance image that may be displayed at S450 according to some embodiments. As described above, a magnetic resonance image exhibits good contrast between the different soft tissues of the body. This contrast facilitates the definition of regions 522, 524, 526 and 528 as shown in image 520. In the present example, region 522 represents the treatment target and regions 524, 526 and 528 represent organs-at-risk (i.e., optic nerves and chiasm).

Next, at S460, a radiation dose associated with each of the plurality of sub-regions is determined based on the second three-dimensional image. For example, the second three-dimensional image may be transferred to the computing device which performed S450, or as in the example of FIGS. 2 and 3, console 260 may operate to perform S450 and S460.

Continuing with the present example, image 530 of FIG. 5 is a slice of a three-dimensional cone beam CT image acquired at S440. Contours 532, 534, 536 and 538 are graphically overlaid onto image 530 to illustrate the sub-regions defined at S450. The registration of S430 facilitates accurate positioning of the contours upon image 530. Further feature-based registration may be employed to ensure proper alignment of the two image data sets.

Image 540 illustrates calculated doses corresponding to a given one or more treatment beams within the patient volume. The dose calculations use the electron density information of image 530, and are performed with respect to sub-regions 532, 534, 536 and 538. Lastly, image 550 illustrates the overlay of the calculated dose information on magnetic resonance image 510. With the doses and regions of interest now known, a clinician may use images 550 and/or 540 to generate a treatment plan as is known in the art.

It is noted that the above process eliminates the need for a separate CT scanner to obtain electron density data. In addition, when megavoltage radiation is used to acquire the cone beam CT image, the above process provides for more accurate dose calculations than systems which use conventional CT images to calculate doses.

In contrast to systems mentioned in the above Background, some embodiments only require the definition of sub-regions including targets and organs-at-risk. Additional tissues, such as bone, need not be defined. Moreover, actual electron density information, rather than default values, is provided for dose calculation.

In some embodiments, another three-dimensional image is acquired using positron emission tomography (PET). PET imaging includes detection of pairs of gamma rays emitted indirectly by a positron-emitting radionuclide (tracer), which is introduced into the body on a biologically-active molecule. The detected pairs are used to construct a three-dimensional image of tracer concentration within the patient volume. Depending on the tracer used, the concentrations may represent tissue metabolic activity. This PET image is used at S450 in combination with the three-dimensional magnetic resonance image to assist in defining the sub-regions.

According to some embodiments, S440 is executed during a collision test that typically precedes generation of a treatment plan. In this regard, after magnetic resonance imaging, a clinician may be able to estimate how a patient should be positioned during radiation treatment, as well as position of a treatment table. Accordingly, a collision test may be performed by rotating the gantry completely around the patient and table to determine if any gantry angles are unusable due to potential collisions. By performing S440 during such a test, conventional treatment workflow may be substantially maintained while experiencing the benefits noted herein.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   acquiring a first three-dimensional image of a patient volume using a magnetic resonance imaging scanner;
   recording a treatment isocenter of the patient volume based on the first three-dimensional image;
   registering the treatment isocenter of the patient volume with an isocenter of a linear accelerator;
   acquiring a second three-dimensional image of the patient volume using cone beam radiation emitted by the linear accelerator while the treatment isocenter of the patient volume is registered with the isocenter of the linear accelerator;
   defining a plurality of sub-regions within the patient volume based on the first three-dimensional image;
   determining a radiation dose associated with each of the plurality of sub-regions based on the second three-dimensional image, the determining of the radiation dose associated with each of the plurality of sub-regions including:
      overlaying contours illustrative of the plurality of sub-regions from the first three-dimensional image of the patient volume onto the second three-dimensional image of the patient volume, wherein the contours are aligned with the second three-dimensional image based on the registration of the treatment isocenter of the patient volume with the isocenter of the linear accelerator;
      calculating the radiation dose associated with each of the plurality of sub-regions using electron density information of the second three-dimensional image; and
   generating a radiation treatment plan based on an overlay of a representation of the calculated radiation dose for each of the plurality of sub-regions onto the first image.

2. The method according to claim 1, further comprising:
   acquiring a third three-dimensional image using a positron emission tomography scanner,
   wherein generating the radiation treatment plan based on the first image and the second image comprises generating the radiation treatment plan based on the first image, the second image and the third image.

3. The method according to claim 1, wherein the cone beam radiation emitted by the linear accelerator comprises megavoltage radiation.

4. The method according to claim 1, wherein the cone beam radiation emitted by the linear accelerator comprises kilovoltage radiation.

5. The method according to claim 1, wherein acquiring the second three-dimensional image of the patient volume using cone beam radiation emitted by the linear accelerator comprises:
   acquiring at least one projection image by positioning an imaging panel of the linear accelerator so that a central ray of cone beam radiation emitted from the linear accelerator does not intersect the center of the imaging panel.

6. A non-transitory computer-readable medium storing processor-executable program code executable to:
   acquire a first three-dimensional image of a patient volume using a magnetic resonance imaging scanner;
   record a treatment isocenter of the patient volume based on the first three-dimensional image;
   register the treatment isocenter of the patient volume with an isocenter of a linear accelerator;
   acquire a second three-dimensional image of the patient volume using cone beam radiation emitted by the linear accelerator, while the treatment isocenter of the patient volume is registered with the isocenter of the linear accelerator;
   define a plurality of sub-regions within the patient volume based on the first three-dimensional image;
   determine a radiation dose associated with each of the plurality of sub-regions based on the second three-dimensional image, the determining of the radiation dose associated with each of the plurality of sub-regions including:
      overlay contours illustrative of the plurality of sub-regions from the first three-dimensional image of the patient volume onto the second three-dimensional image of the patient volume, wherein the contours are aligned with the second three-dimensional image based on the registration of the treatment isocenter of the patient volume with the isocenter of the linear accelerator;
      calculate the radiation dose associated with each of the plurality of sub-regions using electron density information of the second three-dimensional image; and
   generate a radiation treatment plan based on an overlay of a representation of the calculated radiation dose for each of the plurality of sub-regions onto the first image.

7. The medium according to claim 6, the program code further executable to:
   acquire a third three-dimensional image using a positron emission tomography scanner,
   wherein generation of the radiation treatment plan based on the first image and the second image comprises generation of the radiation treatment plan based on the first image, the second image and the third image.

8. The medium according to claim 6, wherein the cone beam radiation emitted by the linear accelerator comprises megavoltage radiation.

9. The medium according to claim 6, wherein the cone beam radiation emitted by the linear accelerator comprises kilovoltage radiation.

10. The medium according to claim 6, wherein acquisition of the second three-dimensional image of the patient volume using cone beam radiation emitted by the linear accelerator comprises:
    acquisition of at least one projection image by positioning an imaging panel of the linear accelerator so that a central ray of cone beam radiation emitted from the linear accelerator does not intersect the center of the imaging panel.

11. A system comprising:

a magnetic resonance imaging scanner to acquire a first three-dimensional image of a patient volume;

a processor to record a treatment isocenter of the patient volume based on the first three-dimensional image, wherein the treatment isocenter of the patient volume is registered, by the processor, with an isocenter of the linear accelerator;

a linear accelerator to emit cone beam radiation to acquire a second three-dimensional image of the patient volume while the treatment isocenter of the patient volume is registered with the isocenter of the linear accelerator;

wherein the processor is further adapted to:
define a plurality of sub-regions within the patient volume based on the first three-dimensional image;
determine a radiation dose associated with each of the plurality of sub-regions based on the second three-dimensional image, the determining of the radiation dose associated with each of the plurality of sub-regions including:
overlay contours illustrative of the plurality of sub-regions from the first three-dimensional image of the patient volume onto the second three-dimensional image of the patient volume, wherein the contours are aligned with the second three-dimensional image based on the registration of the treatment isocenter of the patient volume with the isocenter of the linear accelerator;
calculate the radiation dose associated with each of the plurality of sub-regions using electron density information of the second three-dimensional image; and
generate a radiation treatment plan based on an overlay of a representation of the calculated radiation dose for each of the plurality of sub-regions onto the first image.

12. The system according to claim 11, further comprising:
a positron emission tomography scanner to acquire a third three-dimensional image,
wherein generation of the radiation treatment plan comprises generation of the radiation treatment plan based on the first image, the second image and the third image.

13. The system according to claim 11, wherein the cone beam radiation emitted by the linear accelerator comprises megavoltage radiation.

14. The method according to claim 1, wherein registering the treatment isocenter of the patient volume with the isocenter of the linear accelerator further comprises placing the treatment isocenter at a known distance and direction from the isocenter of the linear accelerator.

* * * * *